United States Patent [19]
Nishida et al.

[11] Patent Number: 5,149,648
[45] Date of Patent: Sep. 22, 1992

[54] ENZYMES EMPLOYED FOR PRODUCING PULPS

[75] Inventors: Tomoaki Nishida, Ibaraki; Yoshinori Kashino, Tsukuba; Akio Mimura, Tsukuba; Yoshimasa Takahara, Tsukuba; Kokki Sakai, Fukuoka, all of Japan

[73] Assignee: Kabushiki Kaisha Kobe Seiko Sho, Kobe, Japan

[21] Appl. No.: 651,632

[22] Filed: Feb. 6, 1991

Related U.S. Application Data

[62] Division of Ser. No. 493,778, Mar. 15, 1990, Pat. No. 5,081,027.

[30] Foreign Application Priority Data

Mar. 16, 1989 [JP] Japan ................................. 1-62162
Mar. 29, 1989 [JP] Japan ................................. 1-74930

[51] Int. Cl.$^5$ .......................... C12P 1/02; C12P 7/00; C12R 1/645
[52] U.S. Cl. ........................ 435/192; 435/41; 435/132; 435/147; 435/156; 435/278; 435/911
[58] Field of Search .................. 435/41, 192, 147, 156, 435/278, 132, 911

[56] References Cited

U.S. PATENT DOCUMENTS

| | | |
|---|---|---|
| 3,962,033 | 6/1976 | Eriksson et al. |
| 4,106,989 | 8/1978 | Komura et al. |
| 4,447,530 | 5/1984 | Young |
| 4,687,745 | 8/1987 | Farrell |
| 4,698,305 | 10/1987 | Hansson |
| 4,830,708 | 5/1989 | Paice et al. |
| 4,889,807 | 12/1989 | Buswell et al. ............ 435/192 |
| 4,891,320 | 1/1990 | Aust et al. |
| 4,960,699 | 10/1990 | Wood et al. ............ 435/192 |

FOREIGN PATENT DOCUMENTS

| | | |
|---|---|---|
| 0371712 | 6/1990 | European Pat. Off. ............ 435/192 |
| 63-137672 | 6/0988 | Japan . |
| 3447410 | 7/1985 | Japan ............ 435/192 |
| 1242577 | 10/1986 | Japan ............ 435/192 |
| 61-281668 | 6/1988 | Japan . |
| 62-210313 | 3/1989 | Japan . |
| 62-210314 | 3/1989 | Japan . |
| 2072875 | 3/1990 | Japan ............ 435/192 |

OTHER PUBLICATIONS

J. Biochem. 92, 531-539 (1982) Aibara et al.
Shannon et al. "Jour. Biol. Chem". vol. 241, No. 9, pp. 2166-2172 May 10, 1966.
Biotech Abs. 89-0923 Farrell et al (EMTED2) Enzyme Microb. Tech. (1989) 11,6, 322-28.
Abstract (Biotech Abs 87-04539)Leisola et al. (JBCHA3) J. Biochem (1987) 262,419-24.
Wood Pulp Technology Times, Hisao Ishikawa, 5, 1-10 (1983).
Science, M. Tien et al, 221, 661 (1983).
Mokuzai Gakkaishi, N. Morohashi, 33, 743 (1987).
FEMS Microbial Lett., S. D. Haemmerl et al, 35, 33 (1986).

*Primary Examiner*—Herbert J. Lilling
*Attorney, Agent, or Firm*—Oblon, Spivak, McClelland, Maier & Neustadt

[57] ABSTRACT

According to this invention, pulps can be produced in high yields while saving energy by previously fiberizing wood chips used as the original material and then treating with a microorganism having a high lignin-degrading activity and a low fiber-degrading activity upon the wood.

In addition, new lignin-degrading enzymes produced by a microorganism used in this invention were identified.

2 Claims, 5 Drawing Sheets

ENZYMES EMPLOYED FOR PRODUCING PULPS

This is a division of application Ser. No. 07/493,778, filed on Mar. 15, 1990, now U.S. Pat. No. 5,081,027.

BACKGROUND OF THE INVENTION

1. Field of the Invention

This invention relates to a method for producing pulps, and more specifically, to a method for producing pulps for various uses by previously fiberizing wood chips used as the original material and then degrading lignin contained in the fiberized wood, at various degree of lignin-degradation, by a microorganism having a high lignin-degrading activity and a low fiber-degrading activity, a culture solution of the microorganism or a substance obtained by treating the solution.

This invention enables energy-saving and high-yield production of pulps and therefore plays an important role in industrial application using a so-called lignocellulose-system biomass.

2. Description of the Prior Art

Pulps are mainly produced from wood and are roughly divided into chemical pulps which do not contain lignin almost entirely, semichemical pulps which contain a small amount of lignin and mechanical pulps which have compositions almost similar to that of wood and contain a large amount of lignin. Chemical pulps and semichemical pulps are produced by decomposing lignin contained in wood, therefore, lignin-degradation by a microorganism enables pulps having nearly the same composition as chemical and semichemical pulps to be produced.

However, as any microorganism having a high lignin-degrading activity and a low fiber-degrading activity has not been isolated up to now, it is the present situation that "it seems impossible to produce a pulp like a chemical pulp from which lignin has sufficiently been decomposed" (Hisao Ishikawa: Wood Pulp Technology Times, 5, 1-10 (1983)).

PROBLEMS TO BE SOLVED BY THE INVENTION

As seen above, the prior art of producing pulps using lignin-degrading fungi has not been put to practical use because of the very low lignin-degrading ability of the fungus used.

Moreover, only up to several % of the lignin could be degraded from wood chips during several-month treatment partly due to the low lignin-degrading activity and therefore it was absolutely impossible to produce any pulp of the chemical pulp level.

MEANS TO SOLVE THE PROBLEMS

This invention was achieved by solving these problems at a stroke in order to industrially produce pulp for various purposes in high yields while saving energy.

Considering the very low lignin-degrading ability of the fungi conventionally used, the inventors systematically screened lignin-degrading fungi having high lignin-degrading ability at first in order to achieve this invention.

Specifically, the inventors collected sources for isolating lignin-degrading fungi widely from Japanese forest and the like, efficiently isolated wood-rotting fungi from samples such as decayed wood by using a method for isolating wood-rotting fungi which the inventors had previously invented (the method of using an agar medium containing wood powder as the only nutrition source, Japanese Patent Laid-Open No. 63-137672) and efficiently selected the lignin-degrading fungi alone from the wood-rotting fungi isolated by the above method by using a method for accurately and efficiently selecting lignin-degrading fungi alone which the inventors had previously invented (Japanese Patent Application Nos. 62-210313 and 62-210314). Using these new test methods in combination made it possible to efficiently examine vast numbers of isolation sources in a short time.

Using these new test methods in combination finally resulted in the inventors' success in newly isolating, from vast numbers of isolation sources, new lignin-degrading fungi having very high lignin-degrading activities and low fiber-degrading activities, that is to say, intended lignin-degrading fungi. The thus newly isolated lignin-degrading fungi were named NK-1148 strain and NK-729W strain and are committed to the care of the Microbial Engineering Institute as FERM BP-1859 and FERM BP-1860 respectively.

Despite the success in isolating lignin-degrading fungi, that is to say intended microorganisms, after further study continued to achieve the above object of this invention, the inventors found it also necessary to study two factors which are the shape of wood material which lignin-degrading fungi are made to act and the degree of lignin-degradation by lignin-degrading fungi.

After further earnest study of the newly noticed above two factors, the inventors found that wood chips used as the original material should be fiberized by pretreatment and that the degree of lignin-degradation by microorganisms should be 75% or above in producing pulps of the level of chemical pulps, 35-75% in producing those of the level of the semichemical pulps and 2-35% in producing those of the level of the mechanical pulps currently industrially manufactured. This led to completion of this invention.

SUMMARY OF THE INVENTION

This invention relates to a new method for producing pulps which is characterized not only by newly devised and adopted use of fiberized woods prepared from wood sources such as wood chips instead of conventional use of these sources as they are, use of newly isolated lignin-degrading fungi and specification of the degree(s) of lignin-degradation by microorganisms but also by organically combined use of these compositions.

Since only a greatly shortened period is required for lignin-degradation in this invention as compared to conventional use of wood chips because a lignin-degrading fungus, its culture product and/or a substance obtained by treating the product can more easily penetrate into the wood tissue of fiberized woods, this invention can solve the problem of the prior art of requiring a long period for lignin-degradation.

Furthermore, since a microorganism having excellent lignin-degrading ability and capable of selectively degrading lignin is used in this invention, it can also solve the disadvantage of the prior art that "it seems impossible to produce pulps of the chemical pulp level".

BRIEF DESCRIPTION OF THE DRAWINGS

FIG. 1 indicates reactivities of dioxane lignin with the new lignin-degrading enzymes of this invention, F-1, F-2 and F-3 in FIGS. 1a, 1b and 1c, respectively;

FIG. 2 indicates optimum pH levels for F-1, F-2 and F-3 in FIGS. 2a, 2b and 2c, respectively;

FIG. 3 indicates enzyme stabilities at various pH levels in FIGS. 3a, 3b and 3c;

FIG. 4 indicates optimum temperatures for the enzymes in FIGS. 4a, 4b and 4c; and FIG. 5 indicates enzyme stabilities at various temperatures in FIGS. 5a, 5b and 5c.

DETAILED DESCRIPTION OF THE INVENTION

In this invention in which wood sources such as wood chips are previously fiberized, it is recommended to prepare fiberized woods at a consumption power of about 70 KWH/wood(t) using an equipment such as a refiner which is used in the current wood pulp industry. Although the consumption power required for preparing fiberized woods varies acccording to the type of an equipment, treatment conditions and similar factors, it is desirable to prepare fiberized woods without causing any fiber cutting while restricting the consumption power to the minimum necessary limit.

NK-1148 strain is an example of those microorganisms having excellent lignin-degrading ability and selectively degrading lignin which can be used in this invention.

NK-1148 strain is a potent lignin-degrading fungus isolated after screening microorganisms capable of efficiently and selectively degrading lignin by the method previously invented by the inventors (Japanese Patent Laid-Open No. 63-137672) and the like.

NK-1148 strain has various mycological characteristics such as follows.

1) State of Growth in Various Media

| Type of Medium | State of Growth |
| --- | --- |
| Malt extract agar medium | +++ |
| Potato-glucose agar medium | +++ |
| Czapek's agar medium | + |
| Sabouraud's agar medium | ++ |
| Synthesized mucor agar medium | ++ |
| YpSs agar medium | +++ |
| Glucose-dried yeast agar medium | +++ |

Note 1) pH of the medium: 5.0 (before sterilization by an autoclave)
Note 2) Culture conditions: 28° C. × 7 days
Note 3) States of growth
weak: +
medium: ++
abundant: +++

2) Physiological and Morphological Properties (1) pH range for the growth (Cultivation in a potato-glucose agar medium at 28° C. for 4 days)

Grows at pH levels near 3-9, does not grow at pH 2 and pH 10 and the optimum pH is near 4-6.

(2) Temperature range for the growth (Cultivation in a potato-glucose agar medium at pH 5 for 4 days)

Grows at temperatures near 10°-45° C., does not grow at 50° C. and the optimum temperature is near 28°-37° C.

(3) Phenol oxidase reaction (Cultivation at 28° C. for 4 days)

Shows weak or negative.

(4) Morphology of colony (Cultivation in a potato-glucose agar medium at pH 5 at 28° C. for 4 days)

White and felt-like.

NK-1148 strain not only is superior in the lignin-degrading activity to fungi of genus Coriolus and genus Phanerochaete which are particularly well-known as lignin-degrading fungi but also has remarkable selectivity of lignin-degradation. This fungal strain is recognized as a new fungal strain named NK-1148 strain and is committed to the care of the Microbial Engineering Institute of the Industrial Technology Board as BP-1859.

It is recommended that a lignin-degrading microorganism, a culture solution of a lignin-degrading microorganism or a substance obtained by treating the solution be added to a medium containing fiberized woods and then the mixture be treated at a temperature near 20°-35° C. for a prescribed period to degrade lignin. It is recommended that the mixture be treated for such a prescribed period that the degree of lignin-degradation becomes 75% or above in producing pulps of the chemical pulp level and 35% or above and less than 75% in producing pulps of the semichemical pulp level. The degree of lignin-degradation may be 2% or above and less than 35% in producing pulps of the mechanical pulp level.

Although mixtures of mycelia and culture solutions obtained by culturing lignin-degrading fungi are widely referred to as culture products of lignin-degrading fungi, mycelia separated from culture products of fungi, their residues and culture solutions from which all solids have been removed can also be used in this invention. All substances obtained by concentrating, thickening, drying or diluting the above culture products are referred to as substances obtained by treating culture products.

Examples of this invention are described in the following.

EXAMPLE 1

250 ml of water was added to each of 100 g of fiberized beech wood by a double disc refiner (70 KWH/wood(t) and 100 g of beech wood chip before fiberizing, respectively. After the mixture was sterilized at 120° C. for 15 minutes, NK-1148 strain (FERM BP-1859) was inoculated into the mixture and was cultured at 28° C. for 1-12 weeks.

The Klason lignin content of fiberized beech wood and chip before and after culture was determined according to JIS P8008-1961 to calculate Klason lignin loss.

The results are shown in Table 1.

TABLE 1

| Period of Cultivation (weeks) | Wood Shapes and Klason Lignin Losses | |
| --- | --- | --- |
| | Klason Lignin Loss | |
| | Fiberized Wood | Chip |
| 0 | 0% | 0% |
| 2 | 30 | 4 |
| 4 | 58 | 6 |
| 8 | 79 | 13 |
| 12 | 88 | 21 |

From the results shown in the above Table 1, it is seen that lignin-degradation is markedly improved by fiberizing wood chips.

EXAMPLE 2

After 250 ml of water was added to 100 g of fiberized beech wood treated using a double disc refiner (70 KWH/wood(t)) and the mixture was sterilized at 120° C. for 15 minutes, NK-1148 strain (FERM BP-1859)

was inoculated into the mixture and was cultured at 28° C. for 1-8 weeks.

Like in Example 1, in Klason lignin content of fiberized wood before and after cultivation with NK-1148 strain was determined, respectively. Besides, the weights of fiberized wood after being dried at 105° C. were also measured to calculate wood yields.

One hundred grams to beech wood chip were used to make as controls each of a chemigroundwood pulp with a yield of about 85% (CGP; amount of NaOH added: 4%, liquid ratio: 5, treatment temperature: room temperature, treatment time: 20 hours), a semichemical pulp with a yield of about 75% (SCP; amount of $Na_2SO_3$ added: 8%, amount of $Na_2CO_3$ added: 3%, liquid ratio: 6, After 120° C. was maintained for 90 minutes, the temperature was raised to 165° C. in 60 minutes, time during which 165° C. was maintained: 120 minutes) and a chemical pulp with a yield of about 50% (CP; amount of NaOH added: 15%, sulfidity: 25%, liquid ratio: 5, cooking temperature: 170° C., time during which temperature was raised: 90 minutes, time during which 170° C. was maintained: 120 minutes) and then their Klason lignin loss and wood (pulp) yields were determined.

The results are shown in Table 2.

TABLE 2

Klason Lignin Losses and Wood Yields

| | | | Period of Cultivation (weeks) | Klason lignin Loss (%) | Wood yield (%) |
|---|---|---|---|---|---|
| | | | 0 | 0 | 100 |
| This Invention | Treatment with NK-1148 strain | Case 1 | 1 | 16 | 95 |
| | | Case 2 | 2 | 30 | 88 |
| | | Case 3 | 4 | 59 | 76 |
| | | Case 4 | 8 | 79 | 61 |
| Controls | Treatment with chemicals | CGP | | 5 | 85 |
| | | SCP | | 35 | 75 |
| | | CP | | 80 | 50 |

For the same wood yield, the degree of delignification of a fiberized wood treated with NK-1148 strain is higher than that of a wood chip treated with chemicals. Therefore, the strength of a pulp prepared from a fiberized wood treated with NK-1148 strain for 2 weeks was stronger than that of CGP and the strength of a pulp prepared from a fiberized wood similarly treated for 4 weeks was also stronger than that of SCP. The strength of a pulp prepared from a fiberized wood treated with NK-1148 strain for 8 weeks was the same as that of CP.

For the same yield, the strength of a pulp obtained by treatment with a microorganism is stronger than that of a conventional pulp. For the same degree of delignification, the yield of a pulp obtained by treatment with a microorganism is about 20% higher than that of a chemical pulp as clearly seen from Case 4 and is also higher than that of a semichemical pulp as seen from Cases 2 and 3. Furthermore, as in Case 1, despite the high degree of delignification, the yield of a pulp obtained by treatment with a microorganism is higher than that of a mechanical pulp. Thus, higher pulp yields are achieved by treatment with a microorganism, which indicates the superiority of preparing pulps by using a microorganism.

EFFECTS OF THE INVENTION

This invention not only enables pulps to be produced in high yields while extremely saving energy by using a new lignin-degrading fungus and specifying other treatment conditions but also enables pulps for various intended uses to be freely produced.

Furthermore, since lignin contents can be reduced by this invention, it is also possible to produce good quality of pulps similar to chemical and semichemical pulps.

This invention also led us to obtain new lignin-degrading enzymes produced by microorganisms used in this invention.

The aforementioned NK-1148 strain (FERM BP-1859) is a definite example of those fungi producing new lignin-degrading enzymes.

PRIOR ART AND ITS PROBLEMS

Ligninase which is produced by *Phanerochaete chrysosporium* and laccase which is produced by *Coriolus versicolor* are known as lignin-degradation-related enzymes produced by fungi.

Ligninase is mainly characterized in that it is a protein containing protoheme IX and having a molecular weight of about 42,000 and an isoelectric point of about 3 and in that it requires hydrogen peroxide for its enzymatic reaction (M. Tien et al: Science, 221, 661 (1983)).

Meanwhile, laccase is mainly characterized in that it is a protein containing copper and having a molecular weight of about 66,000 and an isoelectric point of about 3 and in that it does not require any hydrogen peroxide for its enzymatic reaction (N. Morohoshi: Mokuzai Gakkaishi, 33, 743 (1987)).

However, it is known that the above two enzymes, although they degrade lignin model compounds by reacting upon them, mainly polymerize macromolecular lignins such as milled wood lignin and dioxane lignin (S. D. Haemmerl et al.: FEMS Microbial Lett. 35, 33 (1986)).

It is well known that microorganisms belonging to white-rot fungi have lignin-degrading activity ("Encyclopaedia Chimica 9", Kyoritsu Syuppan, p. 589-590). Of these fungi, attempts have been made to clarify lignin-degrading enzymes by using *Coriolus versicolor* and *Phanerochaete chrysosporium* because these two fungal strains are conventional representative ones.

However, the above fungal strains produce only 10-15% degradation of wood lignin during culture for several weeks and therefore it is the present situation that no enzymes capable of highly degrading macromolecular lignins are isolated.

This invention is intended to solve the above problems and provides new lignin-degrading enzymes capable of changing macromolecular lignins into smaller molecules or degrading them without polymerizing them.

The inventors succeeded in isolating new lignin-degrading fungi capable of degrading 80% or more of wood lignin by using the previously invented method (Japanese Patent Application No. 61-281668) and the like.

The inventors succeeded in producing and isolating a new lignin-degrading enzyme by using a microorganism having a very high lignin-degrading activity and capable of selectively degrading lignin. The inventors further succeeded in producing a significant amount of a new lignin-degrading enzyme by culturing the fungus in a medium containing a lignin-related substance, that is to say, a medium similar to a natural environment wherein the fungus grows. Thus this invention was completed.

In this invention, lignin-degrading fungus may be cultured either in liquid medium or solid medium, and nutrient sources usually used for culture of microorganisms can widely be used for these media. The carbon sources may be any of those ones capable of being utilized and include glucose, sucrose, lactose and molasses. It is preferable to combine these carbon sources with wood powder or lignin-related substances such as syringylglycerol-β-syringylether, vanillyl alcohol and syringyl alcohol in order to efficiently produce the enzyme of this invention. The nitrogen sources may be any of those nitrogen compounds capable of being utilized and include ammonium dihydrogenphosphate, potassium nitrate, ammonium sulfate, peptone, meat extract and casein hydrolysis products. Salts and vitamins are also used according to necessity. The temperature of cultivation can be appropriately varied within the range wherein the fungus grows and produces this enzyme but is preferred to be near 28°-33° C. The period of cultivation, although it varies according to culture conditions, is 5-10 days for liquid medium and 1-3 months for solid medium. In collecting this enzyme from the thus obtained culture product, since this enzyme is mainly excreted outside mycelia, it is recommended to collect a culture filtrate which is removed mycelia by centrifugation for liquid medium and a solution extracted from the culture product for solid medium, respectively.

It is recommended to purify this enzyme by concentrating the enzyme-containing solution, by salting out it using a soluble salt such as ammonium sulfate without concentrating it or by precipitating the enzyme using a hydrophilic solvent such as acetone.

After the dissolution of the salting-out product or the precipitate in a small amount of water or buffer solution, or the dialysis of the concentrated solution with a semipermeable membrane to remove low molecular weight impurities, the enzyme can be purified by one means or at least two means of a gel filtration, an ion-exchange and a liquid-solid chromatography and the like.

The new lignin-degrading enzyme of this invention is possible to isolate three types of enzyme (F-1, F-2 and F-3) from crude enzyme solution by purification.

Therefore, the lignin-degrading enzymes having molecular weights of about 88,000 and isoelectric points of 2-2.5 which are produced by the microorganism of this invention include a crude enzyme of a new lignin-degrading enzyme, the purified enzymes F-1, F-2 and F-3 and any mixture of these enzymes.

The physical and chemical properties of the enzymes of this invention, F-1, F-2 and F-3 are described in the following.

1. Substrate Specificity (1) The enzymes of this invention, F-1, F-2 and F-3, react upon syringylglycerol-β-syringylether(I) to produce α-syringyloxy-β-hydroxypropiosyringon(II), 2-(2,6-dimethoxyphenoxy)-3-hydroxypropanal(III) and 2,6-dimethoxyphenol(IV).

(2) The enzymes of this invention, F-1, F-2 and F-3, react on syringylglycerol-β-syringylether(I) described above but does not react on 4-O-ethylsyringylglycerol-β-syringylether(V) which has an ethoxy group instead of the phenolic hydroxy group of compound (I).

2. Reaction

Figure 1A:
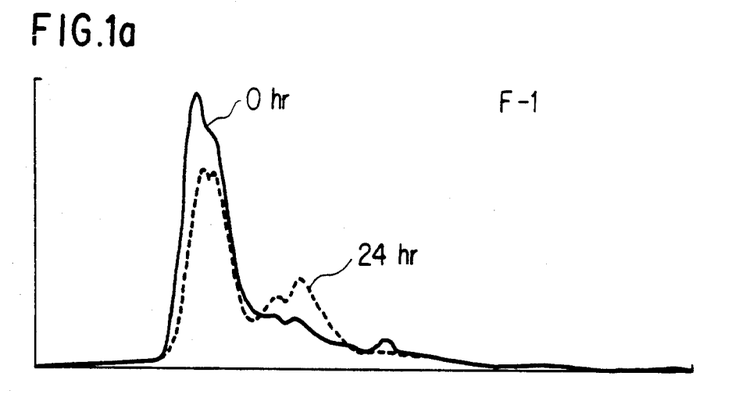
Figure 1B:
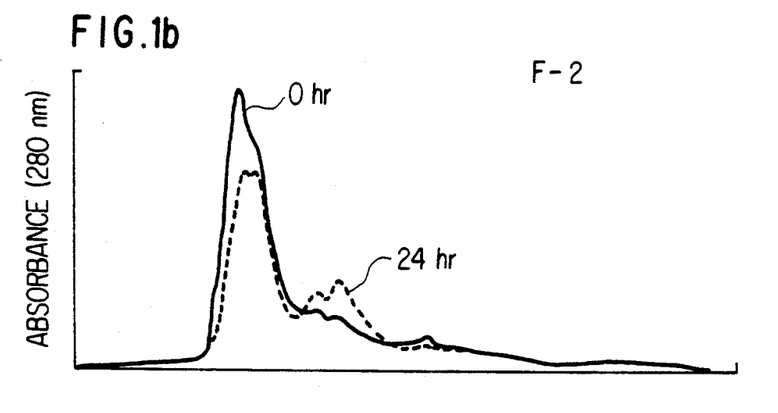
Figure 1C:
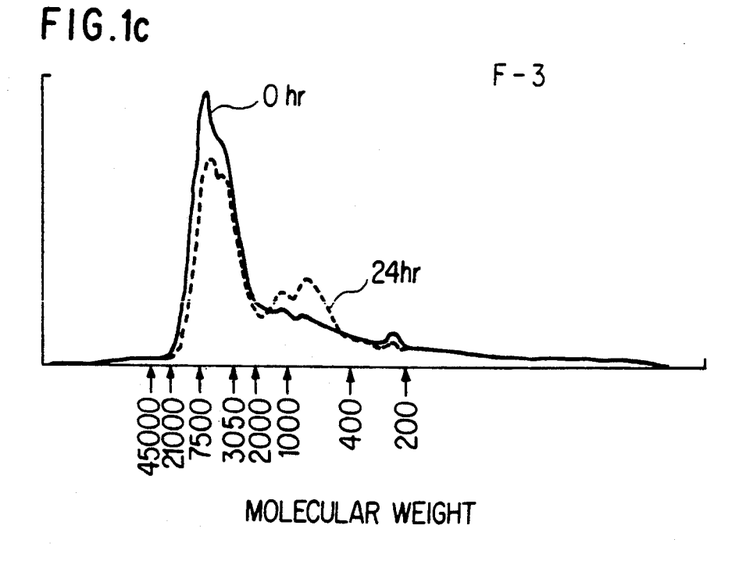

Changes in molecular weight observed when the enzymes of this invention, F-1, F-2 and F-3, were made to react with white birch dioxane lignin are shown in FIGS. 1a, 1b and 1c, respectively. It is seen that all of these enzymes depolymerize and degrade dioxane lignin because the high molecular weight moiety of dioxane lignin is decreased and its low molecular weight moiety is increased. These enzymes can also depolymerize and degrade the milled wood lignin and the lignin contained in waste liquors from cooking or bleaching stage in the production of chemical or semi-chemical pulps.

3. Optimum pH

Figure 2A:
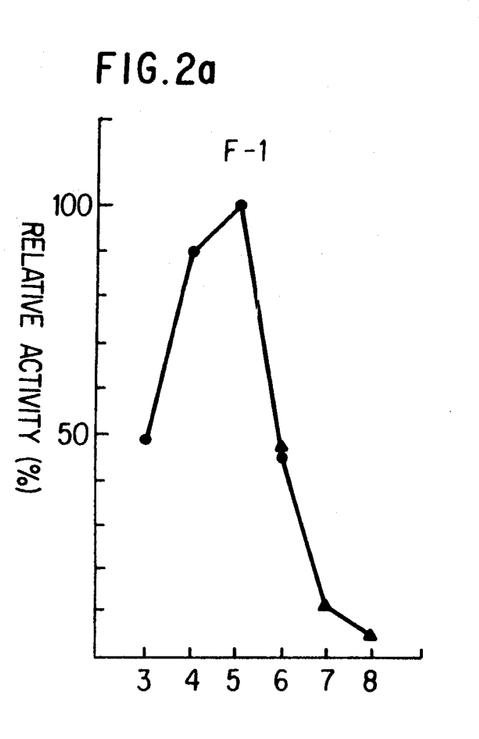
Figure 2B:
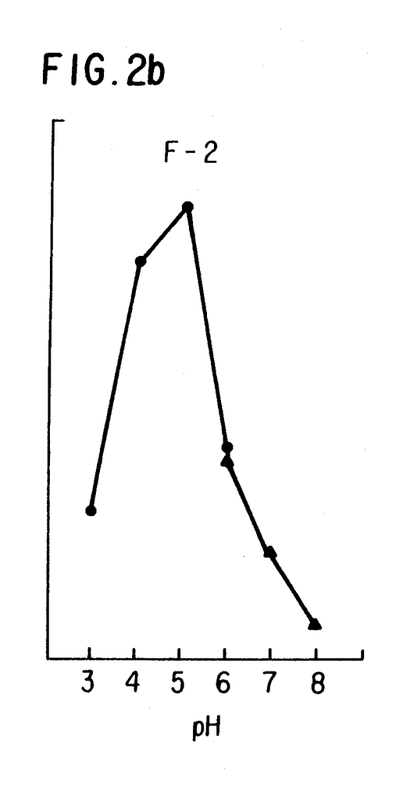
Figure 2C:
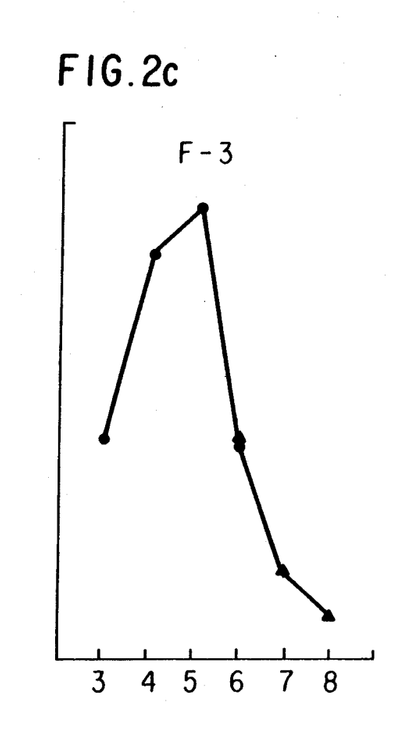

The results of measuring enzyme activities of the enzymes of this invention (F-1, F-2 and F-3) by using 50 mM acetate buffer solutions (pH 3-6) and 50 mM phosphate buffer solutions (pH 5-8) are shown in FIGS. 2a, 2b and 2c, respectively. The optimum pH levels for all of these enzymes are near 4-5.

4. pH Stability

Each of the enzymes of this invention (F-1, F-2 and F-2) were allowed to stand in 50 mM acetate buffer solutions (pH 3-6), 50 mM phosphate buffer solutions (pH 6-8) and 50 mM glycine buffer solutions (pH 7-11)

at 50° C. for 30 minutes and then their enzyme activities were measured.

Figure 3A:
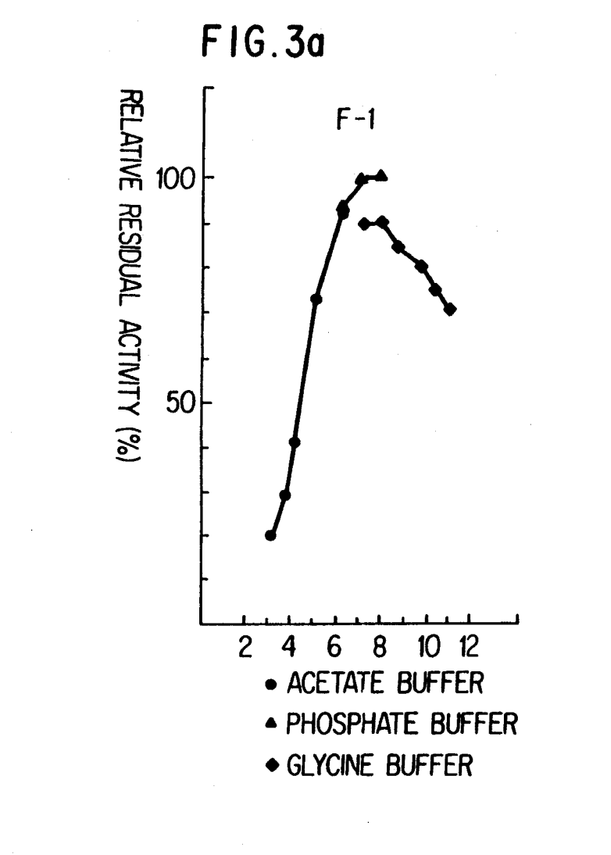
Figure 3B:
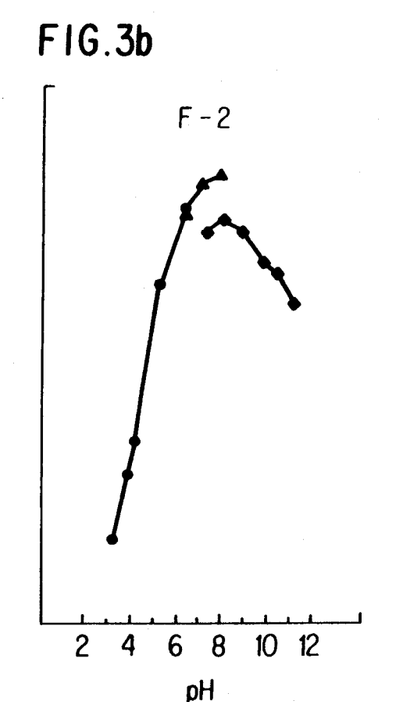
Figure 3C:
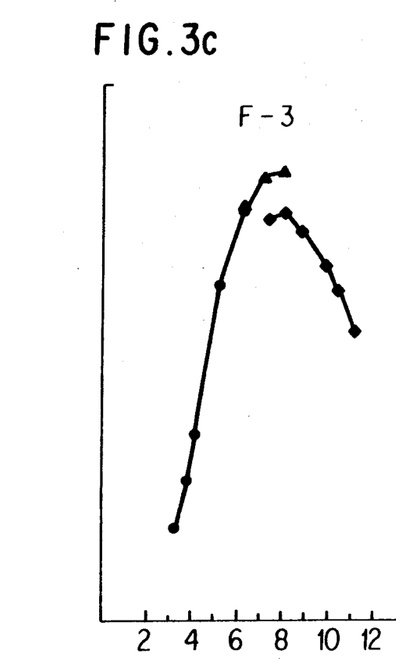

As shown in FIG. 3 (3a, 3b, 3c), these enzymes are stable at pH range from 7 to 8.

5. Optimum Temperature

Figure 4A:
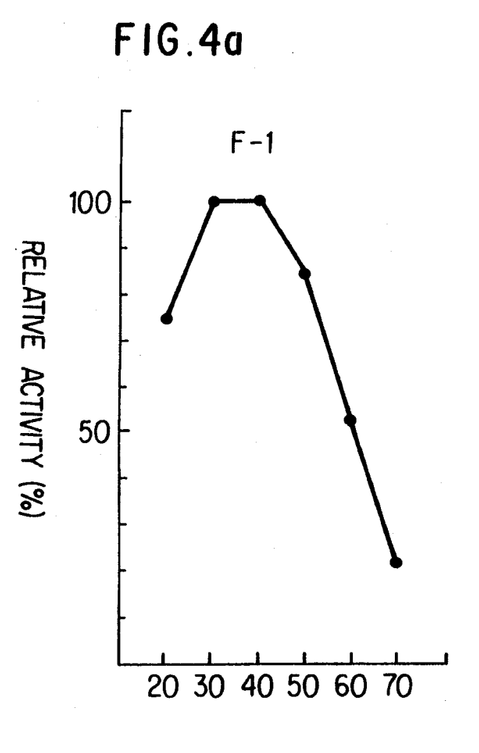
Figure 4B:
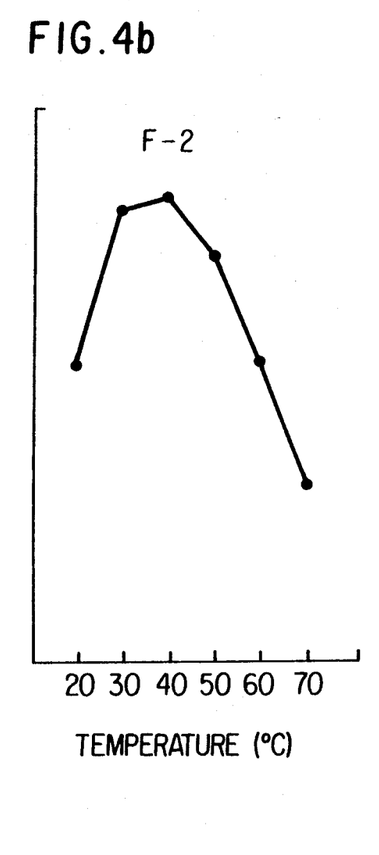
Figure 4C:
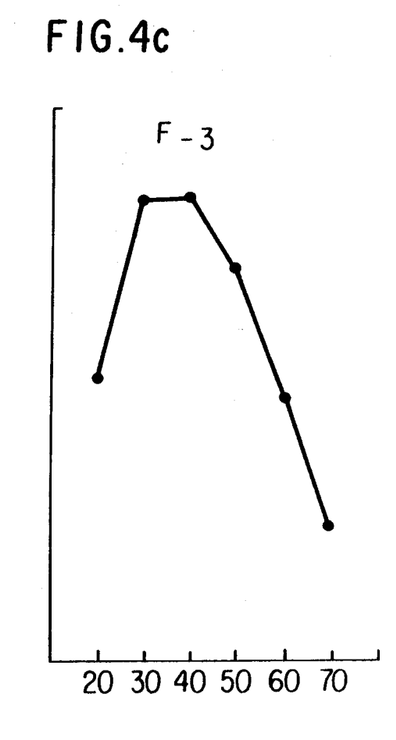

The enzyme activities of the enzymes of this invention (F-1, F-2 and F-3) at various temperatures were measured (FIG. 4) (4a, 4b, 4c).

It is seen that the optimum temperatures for all of these enzymes are near 30°–40° C.

6. Thermal Stability

Each of the enzymes of this invention (F-1, F-2 and F-3) were allowed to stand in a 10 mM phosphate buffer solution (pH 7.0) at each given temperature between 20°–70° C. for 10 min. and then their enzyme activities were measured.

Figure 5A:
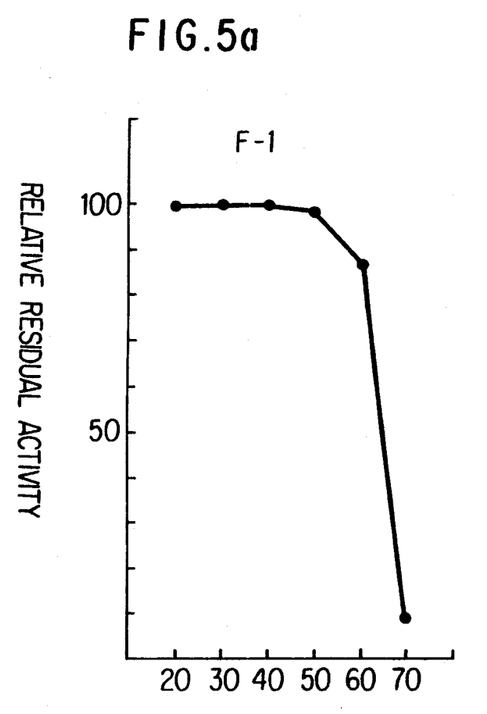
Figure 5B:
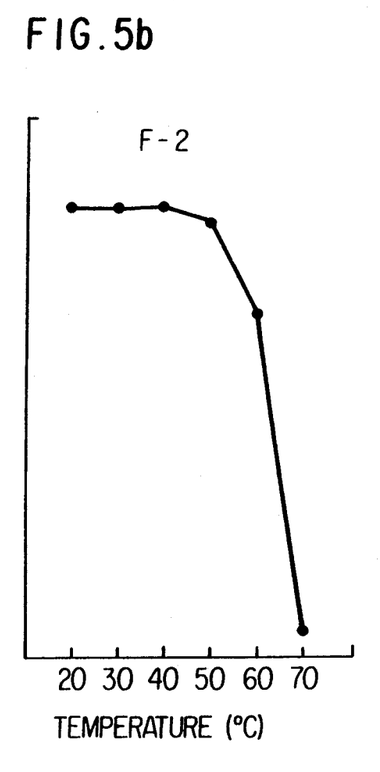
Figure 5C:
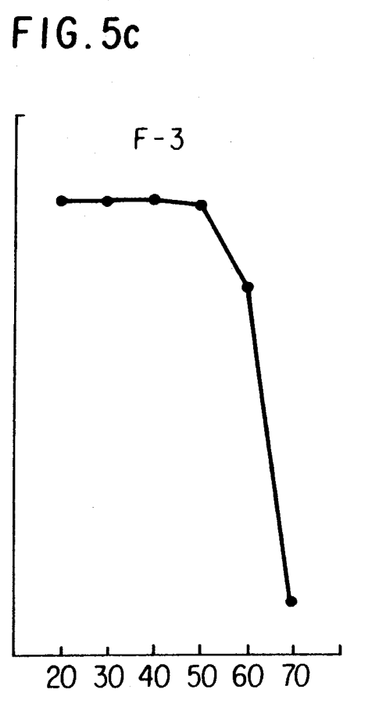

As shown in FIG. 5 (5a, 5b, 5c), the enzymes of this invention are stable at temperatures up to 50° C.

7. Influence of Various Substances

The results of measuring enzyme activities of the enzymes of this invention (F-1, F-2 and F-3) after adding each of various substances are as follows.

| Substance Added | Concentration | Relative Activity F-1 | F-2 | F-3 |
| --- | --- | --- | --- | --- |
| No addition | 0 mM | 100% | 100% | 100% |
| $AlCl_3$ | 1 mM | 61 | 65 | 65 |
| $BaCl_2$ | 1 mM | 93 | 95 | 95 |
| $CaCl_2$ | 1 mM | 94 | 95 | 95 |
| $MgCl_2$ | 1 mM | 94 | 94 | 95 |
| $FeCl_3$ | 0.5 mM | 15 | 31 | 25 |
| $MnCl_2$ | 1 mM | 95 | 95 | 95 |
| $ZnCl_3$ | 1 mM | 94 | 93 | 94 |
| $CoCl_2$ | 1 mM | 97 | 94 | 96 |
| $CuCl_2$ | 1 mM | 102 | 92 | 100 |
| $HgCl_2$ | 1 mM | 11 | 21 | 18 |
| SDS (sodium dodecyl sulfate) | 1 mM | 106 | 101 | 103 |
| Briji-35 (commercial name; surfactant) | 1 PPM | 105 | 100 | 101 |
| 2-Mercapto-ethanol | 1 mM | 10 | 19 | 15 |
| EDTA | 1 mM | 98 | 102 | 101 |
| Cysteine | 1 mM | 11 | 21 | 13 |
| $NaN_3$ | 1 mM | 14 | 23 | 20 |
| KCN | 1 mM | 10 | 17 | 16 |

8. Molecular Weight

The molecular weights of all of the enzymes of this invention, F-1, F-2 and F-3, are about 88,000±5,000 (measured by SDS-polyacrylamide electrophoresis).

9. Isoelectric Point

The isoelectric points of F-1, F-2 and F-3 are about 2.5, 2.2 and 2.0 respectively (determined from elution pHs of chromatofocusing).

10. Assay for Enzyme Activity

20 μl of the enzyme of this invention is made to react with a reaction solution consisting of 10 μl of a 10 mM syringylglycerol-β-syringylether solution which contains a small amount of dioxane and 720 μl of a 50 mM acetate buffer solution (pH 5.0) and increases of absorbance at 300 nm are measured.

Enzyme activity producing a 0.01 increase of absorbance during one minute is supposed to be one unit.

Although this invention is described according to examples in the following, this invention is not restricted to these examples.

EXAMPLE 3

TABLE 3

| Composition of the Medium | |
| --- | --- |
| Glucose | 10.0 g |
| $NH_4H_2PO_4$ | 2.0 g |
| $KH_2PO_4$ | 0.6 g |
| $K_2HPO_4$ | 0.4 g |
| $MgSO_4.7H_2O$ | 0.5 g |
| $CaCl_2$ | 0.1 g |
| Metal salt solution*1 | 1.0 ml |
| Vitamin solution*2 | 5.0 ml |
| Distilled water | 1000 ml |
| pH | 5.5 |

Metal salt solution*1 (g/100 ml)
$FeSO_4.7H_2O:0.1$, $MnSO_4.4-6H_2O:0.1$,
$ZnSO_4.7H_2O:0.05$, $CoCl_2.6H_2O:0.01$,
$CuSO_4.5H_2O:0.01$
Vitamin solution*2 (mg/100 ml)
thiamine hydrochloride:60,
pyridoxine hydrochloride:5,
calcium pantothenate:5,
nicotinic acid:5,
p-aminobenzoic acid:5, folic acid:2.5,
riboflavin:2.5, DL-thioctic acid:2.5,
biotin:1.0, vitamin $B_{12}$:1.25

After one liter of a medium of the composition shown in Table 3 was placed in a 5 liter Erlenmeyer flask and sterilized at 120° C. for 15 minutes, NK-1148 strain (FERM BP-1859) was inoculated into the medium and statically cultured at 28° C. for 7 days. Following that, 20 g of syringyl alcohol was added and the fungus was further cultured at 28° C. for one day.

After cultivation was completed, a culture filtrate obtained by centrifugation was salted out by 90% saturated ammonium sulfate and the resulting substance was dialyzed to obtain a crude enzyme solution containing a new lignin-degrading enzyme.

Subsequently, after the crude enzyme solution was concentrated by ultrafiltration, the concentrated solution was subjected to various types of chromatography using FPLC manufactured by Pharmacia. After the concentrated crude enzyme solution was made to be adsorbed by a Mono Q HR 5/5 column equilibrated with a 10 mM phosphate buffer solution (pH 6.0), the enzyme was eluted with an ionic strength gradient of 10–500 mM phosphate buffer solutions (pH 6.0) (flow rate: 1.0 ml/minute) and active fractions were collected. Next, these fractions were applied to a gel filtration column using a Superose 12HR 10/30 (flow rate: 0.4 ml/minute, eluent: 50 mM phosphate buffer solution pH 7.0). The active fractions were loaded onto a chromatofocusing column using a Mono P HR 5/5 equilibrated with 10 times-diluted PBE 74 (adjusted to pH 3.0 with HCl). After washing the column with the same buffer, the enzyme was eluted with 25 mM formic acid which was adjusted to pH 2.0 with HCl (flow rate: 0.8 ml/minute) and then three types of enzyme, F-1, F-2 and F-3, was(were) purified.

EXAMPLE 4

After 100 ml of a medium of the same composition as that used in Example 3 was placed in a 500 ml Erlenmeyer flask and sterilized at 120° C. for 15 minutes, NK-1148 strain (FERM BP-1859) was inoculated into the medium and cultured at 28° C. for 7 days.

Subsequently, after 0.2% (to the amount of the medium) of either one of syringylglycerol-β-syringylether, syringyl alcohol and vanillyl alcohol which have a phenolic hydroxy group or one of veratryl alcohol and benzyl alcohol which do not have any phenolic hydroxy groups were added, the fungus was further cultured at 28° C. for one day and then enzyme activity was measured.

The effect of lignin-related substances on the enzyme production is shown in Table 4.

TABLE 4

Effect of Lignin-related Substances on the Enzyme Production

| | Enzymatic activity (Unit/ml) |
|---|---|
| Substances having a phenolic hydroxy group | |
| (1) Syringylglycerol-β-syringylether | 3.9 |
| (2) Syringyl alcohol | 4.0 |
| (3) Vanillyl alcohol | 3.95 |
| Substances not having any phenolic hydroxy groups | |
| (1) Veratryl alcohol | 0.05 |
| (2) Benzyl alcohol | 0.01 |
| Control (without any addition) | 0.01 |

As clearly seen from Table 4, the enzyme of this invention is inducibly produced by a substance having a phenolic hydroxy group.

What is claimed is:

1. A purified lignin degrading enzyme F-1, F-2 or F-3, having the following characteristics:
   a) a substrate specificity such that each of F-1, F-2 and F-3 reacts upon syringylglycerol-β-syringylether to produce α-syringyloxy-β-hydroxypropiosyringon, 2-(2,6-dimethoxyphenoxy)-3-hydropropanol and 2,6-dimethoxyphenol;
   b) a substrate specificity such that each of F-1, F-2 and F-3 does not react on 4-O-ethyl-syringylglycerol-β-syringylether;
   c) each of F-1, F-2 and F-3 exhibits a molecular weight of about 88,000±5,000 (SDS-polyacrylamide electrophoresis); and
   d) each of F-1, F-2 and F-3 exhibits an isoelectric point of about 2.5, 2.2 and 2.0, respectively.

2. A purified lignin degrading enzyme F-1, F-2 or F-3, having the following characteristics:
   a) a substrate specificity such that each of F-1, F-2 and F-3 reacts upon syringylglycerol-β-syringylether to produce α-syringyloxy-β-hydroxypropiosyringon, 2-(2,6-dimethoxyphenoxy)-3-hydropropanol and 2,6-dimethoxyphenol;
   b) a substrate specificity such that each of F-1, F-2 and F-3 does not react on 4-O-ethyl-syringylglycerol-β-syringylether;
   c) each of F-1, F-2 and F-3 exhibits a molecular weight change upon reaction with white birch dioxane lignin;
   d) each of F-1, F-2 and F-3 has an optimum pH level for enzyme activity of 4-5;
   e) each of F-1, F-2 and F-3 is stable at a pH of from 7 to 8;
   f) each of F-1, F-2 and F-3 exhibits an optimum temperature of activity ranging from 30°-40° C.;
   g) each of F-1, F-2 and F-3 exhibits a thermal stability up to 50° C. in a 10 mM phosphate buffer solution (pH 7.0);
   h) each of F-1, F-2 and F-3 exhibits a relative activity in the presence of the substances shown in the following table:

| Substance Added | Concentration | Relative Activity | | |
|---|---|---|---|---|
| | | F-1 | F-2 | F-3 |
| No addition | 0 mM | 100% | 100% | 100% |
| AlCl$_3$ | 1 mM | 61 | 65 | 65 |
| BaCl$_2$ | 1 mM | 93 | 95 | 95 |
| CaCl$_2$ | 1 mM | 94 | 95 | 95 |
| MgCl$_2$ | 1 mM | 94 | 94 | 95 |
| FeCl$_3$ | 0.5 mM | 15 | 31 | 25 |
| MnCl$_2$ | 1 mM | 95 | 95 | 95 |
| ZnCl$_3$ | 1 mM | 94 | 93 | 94 |
| CoCl$_2$ | 1 mM | 97 | 94 | 96 |
| CuCl$_2$ | 1 mM | 102 | 92 | 100 |
| HgCl$_2$ | 1 mM | 11 | 21 | 18 |
| SDS (sodium dodecyl sulfate) | 1 mM | 106 | 101 | 103 |
| Briji-35 (commercial name, surfactant) | 1 PPM | 105 | 100 | 101 |
| 2-Mercapto-ethanol | 1 mM | 10 | 19 | 15 |
| EDTA | 1 mM | 98 | 102 | 101 |
| Cysteine | 1 mM | 11 | 21 | 13 |
| NaN$_3$ | 1 mM | 14 | 23 | 20 |
| KCN | 1 mM | 10 | 17 | 16 | i) each of F-1, F-2 and F-3 exhibits a molecular weight of about 88,000±5,000 (SDS polyacrylamide electrophoresis);
   j) each of F-1, F-2 and F-3 exhibits an isoelectric point of about 2.5, 2.2 and 2.0, respectively; and
   k) each of F-1, F-2 and F-3 exhibits a measured increase of absorbance at 300 nm when 20 μl of enzyme reacts with 10 μl of 10 mM syringylglycerol-β-syringylether solution which contains a small amount of dioxane and 720 μl of a 50 mM acetate buffer solution (pH 5.0).

* * * * *